United States Patent [19]

Sorkin

[11] 4,322,354
[45] Mar. 30, 1982

[54] 5-SUBSTITUTED-2-(4-CYANOPHENYL)-1,3,-DIOXANES

[75] Inventor: Howard Sorkin, Berkeley Heights, N.J.

[73] Assignee: Timex Corporation, Waterbury, Conn.

[21] Appl. No.: 136,855

[22] Filed: Apr. 3, 1980

Related U.S. Application Data

[63] Continuation-in-part of Ser. No. 17,635, Mar. 5, 1979, abandoned.

[51] Int. Cl.³ .............................................. C07D 319/04
[52] U.S. Cl. .............................. 260/340.7; 252/299.61
[58] Field of Search ................. 260/340.7; 252/299.61

[56] References Cited

U.S. PATENT DOCUMENTS

| | | | |
|---|---|---|---|
| 2,680,732 | 6/1954 | Martin | 260/340.7 |
| 3,026,328 | 3/1962 | Braun et al. | 260/340.7 |
| 3,912,762 | 10/1975 | Zondler et al. | 260/340.9 |
| 4,066,570 | 1/1978 | Boller et al. | 252/299 |
| 4,085,222 | 4/1978 | Rhodes et al. | 424/278 |
| 4,130,502 | 12/1978 | Eidenschink et al. | 252/299 |
| 4,211,666 | 7/1980 | Inukai et al. | 252/299 |

FOREIGN PATENT DOCUMENTS

| | | |
|---|---|---|
| 139852 | 1/1980 | German Democratic Rep. |
| 139867 | 1/1980 | German Democratic Rep. |
| 2041354 | 9/1980 | United Kingdom ............. 260/340.7 |
| 2044767 | 10/1980 | United Kingdom ............. 260/340.7 |
| 2063288 | 6/1981 | United Kingdom ........... 252/299.61 |
| 2067586 | 7/1981 | United Kingdom . |

OTHER PUBLICATIONS

Mol. Cryst. Liquid Cryst. vol. 56 (Letters), pp. 279-281 Gordon & Breach, Science Publishers, Inc.

Primary Examiner—Ethel G. Love
Attorney, Agent, or Firm—William C. Crutcher; Edward J. Timmer

[57] ABSTRACT

Compounds of the formula:

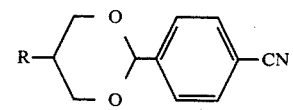

wherein R is an alkyl, alkoxy, aryl, aryloxy, arylester, carboxy or ester derived from carboxy are used as liquid crystal materials in electro-optical displays.

A typical embodiment is 5-butyl-2-(4-cyanophenyl)-1,3-dioxane which has a very low threshold voltage in nematic displays. On rubbed indium oxide surfaces the threshold voltage was 0.6 V using predominately the trans isomer. It was nematic over the range 32.2° C. to 34.6° C.

3 Claims, No Drawings

5-SUBSTITUTED-2-(4-CYANOPHENYL)-1,3,-DIOXANES

This application is a continuation-in-part application of U.S. Ser. No. 17,635 filed Mar. 5, 1979, now abandoned.

BACKGROUND OF THE INVENTION

It is known to use nematic liquid crystal compounds in electrooptic displays. Such displays are utilized in constantly increasing numbers in watches and other instruments. Such devices are well known to those skilled in the art.

One of the problems encountered in the utilization of nematic liquid crystal materials in such displays is the availability of stable low viscosity nematic compounds which are liquid at near room temperatures and have relatively low transition temperatures to make them practical for use in electrooptic display devices. Further, it is desirable that the nematic liquid crystal material require the application of the minimal amount of potential to obtain the desired effect in order to minimize the power requirements in the display device. Only an extremely limited number of nematic liquid crystal compounds thus far known possesses these desired characteristics.

SUMMARY OF THE INVENTION

According to the present invention there is provided a new group of compounds which are stable liquid crystal materials having low viscosity, relatively low transition temperatures. They also have low threshold voltages as determined on rubbed indium oxide surfaces. Such compounds are useful alone or in mixtures in electrooptical liquid crystal display devices which use nematic liquid crystal materials.

The compounds of the present invention are of the formula:

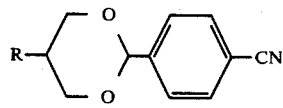

wherein R is an alkyl, alkoxy, aryl, aryloxy, arylester, carboxy or ester derived from carboxy.

Preferably R is a straight chain alkyl, and more particularly a straight chain alkyl of 1 to 8 carbon atoms.

DESCRIPTION OF PREFERRED EMBODIMENTS

The compounds of the present invention where R is alkyl may be prepared as follows:

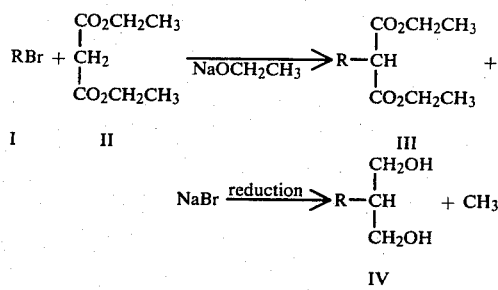

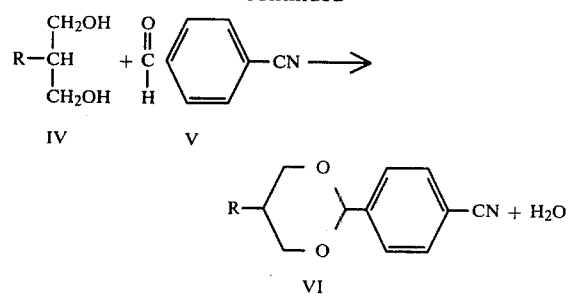

Dimethyl malonate may also be employed in place of diethyl malonate.

The reduction of the malonic acid ester is preferably carried out using a Vitride reducing agent from Eastman Chemicals or with borane-methyl sulfide. Other reducing reagents and methods well known to those skilled in the art may be employed if desired.

The dioxanes of the present invention are obtained as two isomers. Since the trans configuration is elongated, it presumably is the one which accounts for nematic characteristics of the compound.

The following detailed examples are included for purposes of illustration, rather than limitation.

EXAMPLE 1

5-Butyl-2-(4-Cyanophenyl)-1,3-Dioxane

To a five liter, 3-neck round bottom flask fitted with condenser and mechanical stirrer the following are added:

(1) 232 g of sodium methoxide in methanol.

(2) 264.24 g of dimethyl malonate in methanol and stirred for a short period.

(3) 274.06 g of 1-brombutane and 1500 cc of methanol is then added.

The reaction mixture is heated for 65 hours and the resulting dimethyl butylmalonate ester isolated and identified by gas chromatrography.

The dimethyl butylmalonate thus obtained is then reduced. To a 500 ml -3-neck round bottom flask the following are added:

| | | |
|---|---|---|
| (1) | Vitride Solution | 122 ml (.44m) |
| (2) | Benzene Solution | 100 cc |
| | with dimethyl butylmalonate | 37.6g (.2m) |

The addition to the Vitride is carried on over a 20 minute period and then the solution is refluxed for ½ hour, cooled, poured into a separating funnel, and then slowly added to a beaker containing 250 ml of 20% hydrochloric acid standing in ice water. The mixture is maintained 35° C. and stirred until set up.

The mixture is washed with 500 ml methanol and 1000 ml acetone, filtered and a gelatinous precipitate obtained which is dried by azeotroping with benzene. The benzene is stripped and the organic phases combined and vacuum distilled. Product b.p. 100°–104° C./0.75–1.1 mm.

A solution of 6.60 g (0.05 mole) 2-butyl-1,3-propanediol thus obtained and 6.55 g (0.05 mole) p-cyanobenzaldehyde in 60 ml benzen plus a few crystals of p-toluene sulfonic acid is refluxed. Water is removed azeotropically and refluxing continued until no more water forms. The benzene is removed. The residue is vacuum distilled and two fractions are obtained. Their infra-red spectra are identical. Gas chromatography of the fractions gives the following results:

|  | b.p. | Gas Chrom. | Retention Times |
|---|---|---|---|
| FRACT. I | 155°–157° C./0.85 mm | 2.99 | (28%) |
|  |  | 3.45 | (61.9%) |
|  |  | 7.87 | (5.1%) |
|  |  | 9.92 | (5.0%) |
| FRACT. II | 165–167° C./0.5–0.55mm | 2.97 | (24.2%)/ |
|  |  | 3.47 | (75.8%) |

Each fraction is therefore composed of two main components, approximately in the ratio of 1:3.

The trans form of the product is predominate since its formation is less sterically hindered than the cis form.

The two compounds that elute from the gas chromatography at 2.99 min. and 3.45 min. were collected in capillary tubes and transferred to microscope slides using chloroform as the solvent. Evaporation of solvent from peak 1 (2.99 min.) left an isotropic liquid. Evaporation of solvent from peak 2 (3.45 min.) left a nematic liquid crystal with transition temperatures of:

CN (crystal-nematic) = 30.7°–31.0° C.
NL (nematic-isotropic liquid) = 31.4°–32.7° C.

On rubbed indium oxide surfaces spaced ¼ mil apart, $V_{th} = 0.6$ V
$V_{Sat} = 1.3$ V.

Similar values for $V_{th}$, threshold voltage, and $V_{Sat}$, saturation voltage, were obtained on indium oxide surfaces having a $MgF_2$ alignment layer slope evaporated thereon (deposition angle of 30°).

EXAMPLE 2

5-Pentyl-2-(4-Cyanophenyl)-1,3-Dioxane 30.5 g dimethyl malonate is dissolved in 200 ml of methanol. To this is added 500 ml 0.5 M sodium methoxide in methanol, and then a solution of 37.7 g bromopentane in 100 ml of methanol. The solution is stirred and refluxed for 65 hours. A sample analyzed by gas chromatographed shows:

10% bromopentane
22% dimethyl malonate
65% dimethyl pentylmalonate

The methanol is removed on a Roto-vac. The pasty solid remaining is treated with chloroform and separated by filtration. The removal of chloroform leaves a yellow liquid which is then vacuum distilled. A 7 ml forecut is obtained (75°–110° C./12–14 mm Hg). 12.2 g of product is collected at 113°–118° C./14 mm. Gas chromatography shows it to be 98.7% pure.

12.2 g of the dimethyl pentylmalonate are then dissolved in 50 ml benzene. To this is added 25 ml 70% Vitride reducing agent in benzene, in 5 ml increments. The reduction of the ester is followed on gas chromatography. 20 ml of water is added cautiously, and the mixture stirred overnight. 40 ml concentrated hydrochloric acid is added and the benzene layer separated. The aqueous layer is extracted twice with chloroform, the benzene layer dried, and the chloroform layer dried. The aqueous layer is stripped on Roto-vac and the salt boiled with the chloroform second layer.

To a 50 milliliter round bottom flask fitted with magnetic stirrer and condenser, the following components were added:

| (1) benzene | about 25 cc |
| (2) cyanobenzoldehyde | 1.15g |
| (3) 2-pentyl-1,3-propanediol | 1.14g |
| (4) p-toluene sulfonic acid | few crystals |
| (5) calcium sulphate | 2.0g | and refluxed over a weekend. The mixture is cooled. Six percent product is shown by gas chromatography. More paratoluene sulfonic acid is added to the reaction mixture and heating is continued. A precipitate forms when the paratoluene sulfonic acid is added. The $C_5$-diol is stirred overnight in 2% hydrochloric acid and the mixture is then placed in a separating funnel and extracted twice with chloroform and subsequently dired over sodium sulfate with stirring. The chloroform is removed after filterning off the sodium sulfate. Gas chromatography confirms the identification of the end product.

EXAMPLE 3

5-Heptyl-2-(4-Cyanophenyl)-1,3-Dioxane

Using the procedure of the previous example, the following are reacted togehter:

(1) 114.48 g of sodium methoxide
(2) 70.02 g dimethyl malonate are first mixed together and stirred for a short period.

Then there is added 500 cc of methyl alcohol and 95.0 g of n-bromoheptane.

The reaction mixture is heated over the weekend refluxing at 68° C., then cooled and the methyl alcohol stripped on the Roto-vac. The product dimethyl heptyl malonate is taken up in chloroform, the salt filtered off, and chloroform stripped off on the Roto-vac and the product vacuum distilled and identified by gas chromatography.

184 ml Vitride reducing agent are added to a one liter round bottom flask together with 250 ml benzene and the solution brought to reflux. Then the following solution was added:

69.0 g of the above dimethyl heptylmalonate ester in 100 cc benzene.

After addition of the ester solution, the reaction mixture is heated for one hour at reflux.

An additional amount (½) more of Vitride was added and the reaction mixture heated for 40 more minutes.

Finally, after the addition of 20% then 50% hydrochloric acid solution, the pH was brought to 5. The product is pasty and difficult to filter. The organics were removed in a separating funnel. Each half of the water layer was extracted with chloroform, combined and stripped on the Roto-vac. Organics were separated from the extracted water layers and combined, and then stripped on the Roto-Vac.

the heptyl diol obtained is then reacted as follows:

In a 50 ml round bottom flask the following components are combined:

| (1) benzene | 25 ml |
| (2) cyanobenzaldehyde (.01 m) | 1.2g |
| (3) $C_7$ diol from above | 1.74 |
| (4) Paratoluene sulfonic acid | few crystals |
| (5) Calcium sulphate $CaSO_4$ | 2.0g | and refluxed overnight to obtain the desired end product, 5-heptyl-2 (4-cyanophennyl)-1,3-dioxane.

EXAMPLE 4

5-Octyl-2-(4-Cyanophenyl)-1,3 Dioxane

The following are reacted together in a 3-neck round bottom flash fitted with a mechanical stirrer.

1 liter of methanol
216.0 g of sodium methoxide
160.17 g of diethyl malonate.

The foregoing are stirred together for a short time and then 193.13 g of 1-bromo-octane added.

The mixture is heated overnight at reflux, cooled, and the methanol stripped. The product is taken up in chloroform and the sodium bromide salt filtered off. The chloroform is evaporated and the sample distilled.

To a 3-neck, 1 liter round bottom flask and the following components are added:

(1) 500 cc fresh toluene.
(2) 136 g of diethyl octyl malonate ester obtained as described and
(3) 110 ml borane-methyl sulfide which is added dropwise over a one hour period.

The mixture is heated slowly to reflux, and refluxing continued for 12-15 hours. The reaction mixture is then cooled to room temperature and added from a separating funnel to a beaker containing 400 cc of methyl alcohol. After the mixture stands overnight the alcohol is stripped on the Roto-vac.

Ten percent hydrochloric acid in 100 cc of water is added to the diol with stirring. After all of the acid solution has been added over about 15-20 minutes, a gelatinous mass is obtained which is filtered and the diol product isolated as in the foregoing examples.

A single neck 50 cc round bottom flask is charged with:

1.88 g of the octyl diol obtained above;
1.15 g of cyanobenzaldehyde
25 cc of benzene
Few crystals of paratoluene sulfonic acid
2.0 g of calcium sulfate powder.

The mixture is heated for 16 hours at reflux, the product isolated, and identified by gas chromatography.

In the instances of the compounds of Examples 2, 3, and 4, the following melting points and transition temperatures were obtained:

|  | M.P. | CN(CL) | NL (LN) |
|---|---|---|---|
| Example 2 | 53.0° C. | 46.0° C. | 47.5° C. |
| Example 3 | 50.0° C. | (54.1° C.) | (49.8° C.) |
| Example 4 | 47.2° C. | (59.0° C.) | (47.3° C.) |

Compounds of the present invention where R is other than alkyl may be prepared as follows:

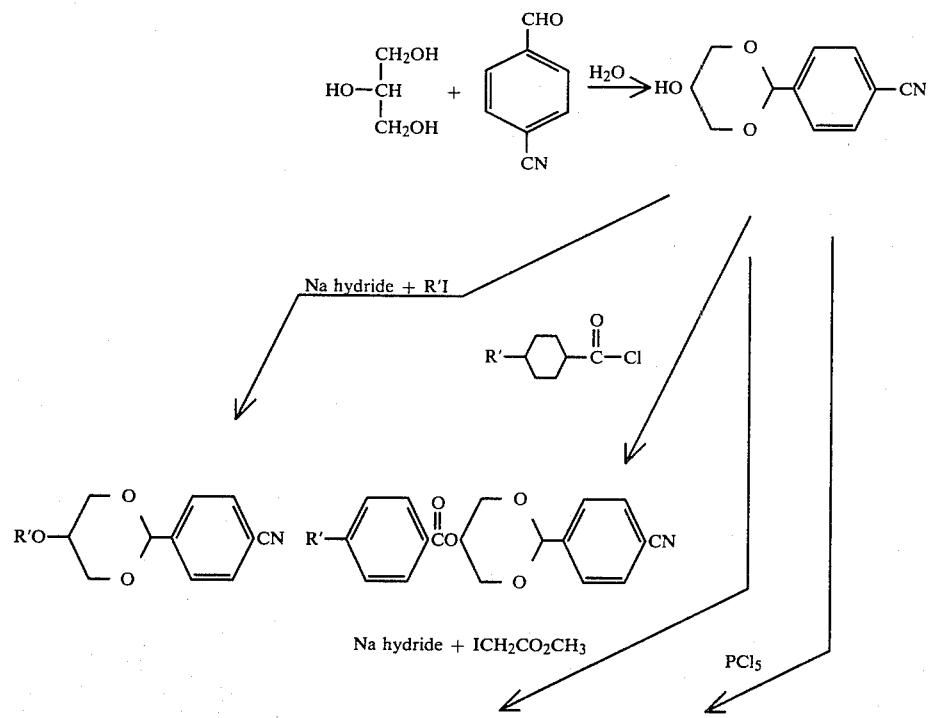

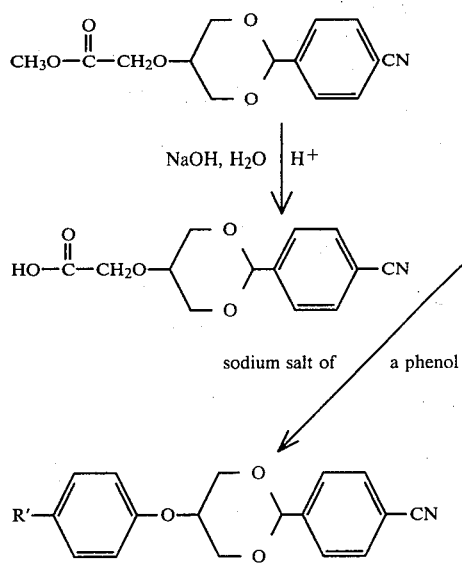

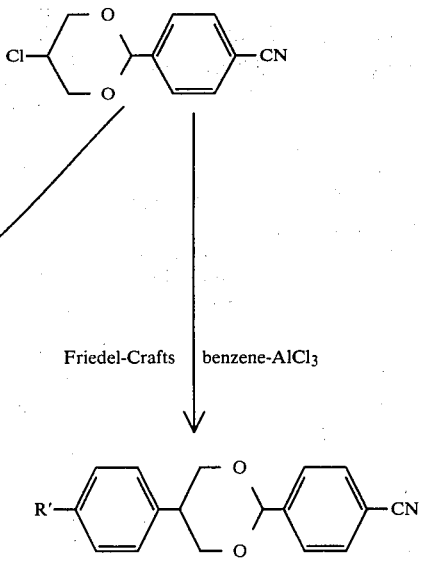

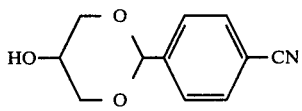

where R' is, for example, alkyl.

From the flow chart, it is apparent that the non-alkyl series of the compounds can be made from the intermediate hydroxy compound,

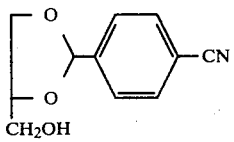

formed from the condensation of glycerol witgh cyanobenzaldehyde, which reaction is known in the art, e.g., see *Rec. Trav. Chem.*, 1942, 61, pp. 831–841. Substitution of cyanobenzaldehyde for benezaldehyde in the known condensation reaction produces the desired intermediate hydroxy compound. For example, 5-hydroxy-2-(4-cyanophenyl)-1,3-dioxane was produced by refluxing a mixture of 55.2 grams glycerol, 750 ml benzene, 78.6 grams cyanobenzaldehyde and a few crystals of p-toluenesulfonic acid and collecting water in a Dean-Stark trap. When no more water evolved, the solution was cooled and washed with 5% aqueous sodium carbonate. The crystals which formed were collected, washed with water and dried to give 5-hydroxy-2-(4-cyanophenyl)-1,3-dioxane. 5-hydroxymethyl-2-(4-cyanophenyl)-1,3 dioxolane:

[structure with CH$_2$OH]

is also formed in this reaction. Since both 5-hydroxy-2-(4-cyanophenyl)-1,3-dioxane and 5-hydroxymethyl-2-(4-cyanophenyl)-1,3-dioxolane can form cis and trans isomers, all four compounds are obtained from the condensation. Recrystallization removes the latter of these compounds and gives a mixture of isomers of 5-hydroxy-2-(4-cyanophenyl)-1,3-dioxane (5.5:1 cis to trans ratio; melting point 124.1°–130.2 C.).

The reaction of this isomer mixture with 4-pentylbenzoyl chloride gives 5-(4'-pentylbenzoxy)-2-(4[11]-cyanophenyl)-1,3 dioxane,

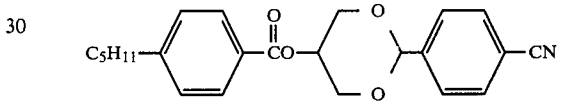

which is exemplary of the arylester (

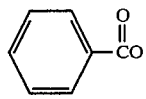

) substituted compounds of the invention. For example, to a solution of 2 grams of 5-hydroxy-2-(4-cyanophenyl)-1,3-dioxane (isomer mixture) in 10 ml pyridine was added a solution of 2 grams p-pentylbenzoyl chloride in 10 ml pyridine. After stirring overnight, the solution was poured into 100 ml water. The solid was collected, washed with water and recrystallized from methanol-water. A second recrystallization of the solid from isopropanol at room temperature yielded a mixture of isomers (3:1 cis to trans) of the compound. Cooling this solvent in the refrigerator gave a second crop of crystals which were essentially pure trans material (31:1 trans to cis). This material is liquid crystalline exhibiting a crystal to nematic transition temperature (C-N) of 101° C. and a nematic to isotropic liquid transition temperature (N-L) of 129° C.

The hydroxy radical of the intermediate compound can be converted to alkoxy or carboxy ester by a variation of the Williamson ether synthesis (*Name Reactions In Organic Chemistry*, A. R. Surrey Co., Academic Press Inc. 1954) as set forth in *Can. J. Chem.*, 1966, 44, pp. 1591–1592, in which sodium hydride and an alkyl iodide are reacted with the intermediate compound to form the alkoxy series while sodium hydride and iodide of an ester are involved in producing the carboxy ester series. The carboxy ester dioxane compounds can be readily hydrolyzed to the corresponding carboxy series by well known methods. The hydroxy radical of the intermediate compounds can also be converted to chloro by reaction with phosphorous pentachloride as is well known and shown in *Compendium Of Organic Synthetic Methods,* I. T. Harrison and S. Harrison, Wiley Interscience (1971) and *J. Chem. Soc.,* 1970, pp. 1124–1125. The chloro intermediate compound can then be converted to the aryl compound by the well known Fridel-Crafts reaction (*Name Reactions In Organic Chemistry,* A. R. Surrey, Academic Press Inc. 1954) or to the aryloxy by reaction with the sodium salt of a phenol in accordance with the aforementioned Williamson ether synthesis (*Name Reactions In Organic Chemistry,* A. R. Surrey; Academic Press Inc. 1954 and *J. Am. Chem. Soc.,* 1947; 69, pp. 2451–2454). In the reactions described in this paragraph it may be necessary to react only predominantly the trans form of the intermediate hydroxy compound. Analytical chromatographic analyses of the isomers of the intermediate compound showing different absorption peaks indicate that use may be made of known preparative liquid chromatographic techniques to effect separation of the trans isomer from the cis isomer.

It should be apparent to those skilled in the art that various changes in form and detail in this invention can be made. It is intended that such changes be included within the spirit and scope of the claims appended hereto.

What is claimed is:

1. A compound of the formula:

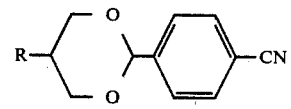

wherein R is alkyl.

2. A compound as claimed in claim 1 where R is a straight chain alkyl.

3. A compound as claimed in claim 2 where R is a straight chain alkyl of 1 to 8 carbon atoms.

* * * * *